United States Patent [19]
Hamawy et al.

[11] Patent Number: 6,150,121
[45] Date of Patent: Nov. 21, 2000

[54] ASSESSING IMMUNOLOGICAL STATE OF TRANSPLANT RECIPIENTS

[75] Inventors: Majed M. Hamawy, Madison; Stuart J. Knechtle, Fitchburg, both of Wis.

[73] Assignee: Wisconsin Alumni Research Foundation, Madison, Wis.

[21] Appl. No.: 09/250,679

[22] Filed: Feb. 16, 1999

[51] Int. Cl.[7] .............................. C12Q 1/68; G01N 33/50
[52] U.S. Cl. ................................................ 435/7.24; 435/6
[58] Field of Search ........................................ 435/6, 7.24

[56] References Cited

U.S. PATENT DOCUMENTS

| | | | |
|---|---|---|---|
| 4,714,674 | 12/1987 | Palladino | 435/18 |
| 4,959,302 | 9/1990 | Cornaby et al. | 435/5 |
| 5,223,396 | 6/1993 | Rothlein et al. | 435/7.21 |
| 5,334,504 | 8/1994 | Wood et al. | 435/7.32 |
| 5,482,841 | 1/1996 | Buelow | 435/7.24 |
| 5,652,337 | 7/1997 | H. Oppermann et al. | 530/350 |
| 5,698,448 | 12/1997 | Soldin | 436/503 |

FOREIGN PATENT DOCUMENTS

WO91/18626  12/1991  WIPO .

OTHER PUBLICATIONS

Lohmann–Matthes et al, Transplantation Reviews, 17, 150–171, 1973.

Mayhew et al, Immunology, 21, 123–136, 1971.

Pierce et al, Transplantation, 27, 156–162, 1976.

Hamburger et al, C.R. Acad. SC. Paris, 275, Series D, 2089–2092, 1972.

T. Mohanakumar et al.,*Tissue–Specific HLA Class 1 Restricted CTL Are A Significant Subpopulation of Graft–Infiltrating Lymphocytes During Rejection*, 29 Transplantation Proceedings—Histopathology 87–88 (1997).

Abstract from Dialog MedLine of T. Fujisawa et al., *Detection of Donor Specific Cytotoxic T Lymphocyte Activity in Lung Grafted Mongrel Dogs*, 30, 37 Nippon Kyobu Geka Gakkai Zasshi 203–207 (1989).

A. Abbas et al., Cellular And Molecular Immunology, pp. 350–351, (W. B. Saunders Company 1994).

R. Moliterno *et al.*, Heat Shock Protein Reactivity Of Lymphocytes Isolated From Heterotopic Rat Cardiac Allografts, 59 Transplantation 598–604 (1995).

*Primary Examiner*—David Saunders
*Attorney, Agent, or Firm*—Quarles & Brady LLP

[57] ABSTRACT

Disclosed herein are methods for monitoring the immunological status of transplant recipients. Fibroblast cells derived from transplanted organs are used in proliferation assays with lymphocytes taken from the recipient after transplantation. The comparison of assay results in the presence of, and in the absence of (or in the presence of reduced levels of) a cytokine growth factor such as interleukin-2, is used to determine whether the organ is being rejected. Also disclosed are kits for practicing these methods.

7 Claims, 2 Drawing Sheets

ASSESSING IMMUNOLOGICAL STATE OF TRANSPLANT RECIPIENTS

STATEMENT REGARDING FEDERALLY SPONSORED RESEARCH

This invention was made with United States government support awarded by the following agency: NIH 5RO1AI40597-02. The United States has certain rights in this invention.

BACKGROUND OF THE INVENTION

The present invention relates to methods for determining the immunological status of transplant recipients (and kits used for such purposes). More particularly, it relates to non-invasive techniques for discriminating between non-rejecting human organ transplant recipients and those experiencing rejection.

Organ transplantation is an important therapeutic option for patients with end-stage organ diseases. Although improved immunosuppressive strategies have dramatically increased the rate of short-term success of such transplants, the rate of long-term transplantation success has not improved as significantly, primarily due to a high incidence of rejection episodes. Rejection episodes, if not quickly diagnosed and treated, often significantly and adversely affect long-term function of the transplanted organs.

Rejection can be detected by observing gross symptoms (e.g. elevated temperature; significant failures of the function of the transplanted organs). However, if one waits for gross symptoms to appear before modifying immunosuppressive therapy, long-term injury may have already occurred to the transplanted organ. Thus, bioassays have been developed to try to detect early stages of rejection episodes. Various bioassays have been developed. See generally U.S. Pat. Nos. 4,959,302; 5,223,396; 5,334,504; and 5,482,841. The disclosure of these publications, and all other publications referred to herein, are incorporated by reference as if fully set forth herein.

Such bioassays are also desirable to render more efficient immunotherapy. In this regard, when doctors have confidence in their ability to spot the early onset of rejection episodes, they are more willing to try to minimize use of immunotherapeutic drugs (and thereby reduce the costs of such drug treatment and the risk of drug-associated side effects).

One existing bioassay approach is to measure general T cell activation by (i) spontaneous blastogenesis in which freshly isolated lymphocytes from the transplant recipient are examined from time to time for [$^3$H] thymidine uptake, and (ii) expression of surface molecules associated with T cell activation such as the receptor CD25. A drawback of this approach is the incidence of false positive results (as such assays do not discriminate well between T cell activation due to rejection and that due to viral or bacterial infection).

False positives can lead to the patient having to undergo unneeded prophylactic drug therapy, as well as unnecessary emotional stress.

Another bioassay approach assesses activation status of donor-specific T cells isolated from graft biopsies. This determination is by the mixed lymphocyte reaction in which lymphocytes isolated from the graft are examined for [$^3$H] thymidine uptake after incubation with irradiated donor lymphoid cells. A variant is a determination by cell-mediated lympholysis in which lymphocytes isolated from the graft are examined for their ability to lyse chromium-labeled donor lymphoblastoid cells. Graft-derived endothelial and epithelial cells have also been used to stimulate recipient lymphocytes isolated from the graft.

Major drawbacks with respect to these assays are that these assays typically use growth factors to propagate and potentiate the responsiveness of recipient T cells, a process that alters T cell responsiveness. This is important because the presence of donor-specific lymphocytes in the organ is not by itself an indicator of rejection, since cellular infiltrates can often be detected in the graft without any signs of pathological changes associated with rejection.

Also, the donor lymphocytes commonly used in these assays to stimulate donor-specific recipient T cells may not bear graft-specific antigens, leading to false negative results. Moreover, as with histological and gene expression analysis, such graft-specific bioassays also require graft biopsies. As a result of these deficiencies, the biological assays that have been commercialized for monitoring transplanted organ rejection status (prior to gross rejection symptoms appearing) have not gained widespread acceptance.

The most dependable tool currently used for diagnosing graft rejection is biopsy histology. However, repetitive biopsy for purposes of monitoring transplant status can be invasive and expensive. Also, this technique can sometimes be too insensitive to detect early, subtle cytopathic processes. Further, reading of histological slides for this purpose requires special expertise to accurately and consistently interpret results, thus raising its cost as well as the risk of occasional improper interpretation.

As such, it can be seen that the need exists for improved bioassay techniques for monitoring the immunological status of human transplant recipients.

BRIEF SUMMARY OF THE INVENTION

In one aspect the invention provides a method for monitoring the immunological status of a human transplant recipient who has received a transplanted organ. As step X, in the presence of a first concentration of an externally supplied quantity of a specified cytokine growth factor, one exposes fibroblast cells derived from the organ to post-transplant lymphocytes from the recipient (other than lymphocytes from the transplanted organ). One then determines the extent to which the step X lymphocytes are immunologically activated by exposure to the step X cells.

Either before or after step X, as step XX, in the absence of an externally supplied quantity of said specified cytokine growth factor, or in the presence of a concentration thereof which is less than that used in step X (e.g. preferably less than half that used), one exposes fibroblast cells derived from the transplanted organ to post-transplant lymphocytes from the recipient (other than lymphocytes from the transplanted organ). One then determines the extent to which the step XX lymphocytes are immunologically activated by exposure to the step XX cells.

One can then determine from the extent to which the activation is greater in step X than in step XX whether the transplanted organ is being rejected by the recipient.

Preferred cytokine growth factors for use in this method are interleukin-2, interleukin-4, and transforming growth factor-$\beta$, albeit interleukin-2 is most preferred.

In preferred forms the lymphocytes are obtained by drawing blood from the recipient (the blood containing peripheral blood lymphocytes). [$^3$H] thymidine uptake can then be used in a proliferation assay to indicate the degree of activation of the lymphocytes by the exposures.

In yet another aspect, the invention provides a kit for monitoring the immunological status of a human transplant recipient. The kit contains a cytokine selected from the group consisting of interleukin-2, interleukin-4 and transforming growth factor-$\beta$, [$^3$H] thymidine, and collagenase (preferably type IV).

Various other techniques besides radioactive uptake can be used to monitor the extent of lymphocyte activation once the exposure has taken place (e.g. cell lysing techniques using chromium labeling; protein tyrosine phosphorylation; and gene expression). However, the radioactive uptake is preferred as counting equipment is available that can accurately and quickly read the radioactive content resulting from each experimental condition.

While preferably a fibroblast monolayer is developed from a segment of the transplanted organ taken prior to transplantation, a biopsy specimen of the transplanted organ can also be obtained after transplantation, with the fibroblast layer being developed therefrom.

It has been surprisingly learned that the degree of activation (e.g. measured by a proliferation assay using radioactive thymidine uptake) of blood lymphocytes from non-rejecting hosts that were exposed to the organ derived fibroblast cells was markedly less in the absence of IL-2 than in its presence. By contrast, activation levels of blood lymphocytes from rejecting patients were much closer in value in the presence and absence of a specified cytokine growth factor. Thus, the relative ratio of assay results in the presence and absence of the specified cytokine growth factor can be used to determine rejection status.

The objects of the present invention therefore include providing:

(a) non-invasive methods for monitoring whether a human transplant recipient is experiencing a rejection episode;

(b) methods of the above kind which can detect such rejection episodes at an early stage;

(c) methods of the above kind which have a low incidence of false positives and false negatives; and (d) kits for practicing such methods. These and still other objects and advantages of the present invention will be apparent from the description which follows. The following description is merely of the preferred embodiments. Thus, the claims should be looked to in order to understand the full scope of the invention.

DESCRIPTION

Overall Approach

Figure 1:
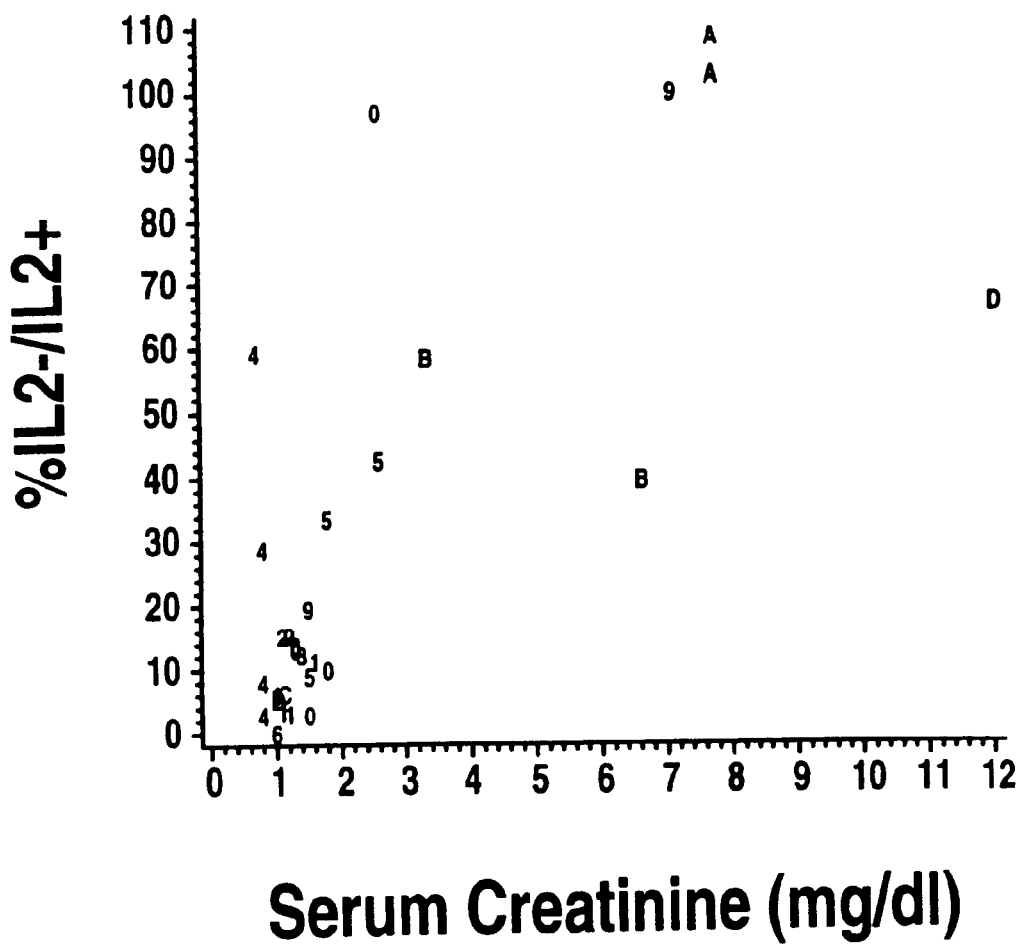
FIG. 1 depicts the % IL-2-/IL-2+ response of peripheral blood lymphocytes obtained from animals plotted against serum creatinine where the response is to donor GDFL cells.

In our assay we obtain a specimen derived from the organ that has been (or is about to be) transplanted, develop a fibroblast-like culture therefrom, and cause cells from that culture to interact with lymphocytes taken from the transplant recipient after transplantation. Specifically, we use graft-derived fibroblast-like (GDFL) cells to detect sensitized allograft-specific cells in the blood (peripheral blood lymphocytes) of the graft recipient. GDFL cells are used as a source for alloantigens and the recipient blood as a source for allograft-specific lymphocytes.

GDFL cells bear MHC class I molecules but not class II. Thus, one theoretical underpinning for the assay is that sensitized allograft-specific lymphocytes in the blood of a rejecting recipient will be activated by the interaction with the alloantigen-MHC class I complex on GDFL cells.

Most importantly, we have found that expressing the results by comparing the lymphocyte response to GDFL cells in the absence of a cytokine growth factor (such as IL-2, IL-4, and transforming growth factor-$\beta$) to the response in the presence of that growth factor allows discrimination between rejecting and non-rejecting transplant recipients. We have also found that the use of GDFL cells instead of donor lymphocytes makes an important difference in the reliability of the assay results.

Briefly, GDFL cells were isolated from biopsies and grown as monolayers in wells of tissue culture plates. Peripheral blood lymphocytes (PBLs) from the recipients were then overlayered on the monolayers in the presence (or absence) of the cytokine growth factor. The cells were then incubated for 3 days. On day 4, the cells were pulsed with [$^3$H] thymidine and the incubation resumed for another 16 hr. [$^3$H] thymidine uptake was used as an indicator of cell activation. The ratio of [$^3$H] thymidine uptake was calculated according to the following equation: (net mean radioactivity count in the absence of cytokine X 100) divided by (net mean radioactivity count in the presence of cytokine).

Detailed Experiments

A. Creation Of Graft-Derived Fibroblast-Like Cell Lines

Our studies have shown that GDFL cells can be isolated from human and rhesus monkey biopsies and can be propagated in culture in a monolayer fibroblast form. As an example, 100 $\mu$l of 1% collagenase(type IV)-RPMI were placed in wells of a 96-well flat-bottom tissue culture plate. The collagenase-RPMI was made by taking 1 gram of collagenase and placing it on the top of 100 ml RPMI (Mediatech, Inc., Herndon, Va.). Collagenase was then allowed to dissolve at room temperature without shaking. The reagent was filtered using 0.22 um filters, and stored at $-80°$ C. until use.

Fine needle aspiration biopsies of donor kidney were immersed in cold RPMI and minced into small pieces using a sharp small scissors. The minced tissues were placed into the collagenase-containing wells. Care was taken to insure that the tissue fits loosely in the well and was completely immersed in the collagenase.

The plates were incubated at 37° C. in a 5% $CO_2$ water-jacketed incubator. At least every sixty minutes the tissues in the wells were teased by aspirating the contents of the well up and down using a pipetman. The process was continued until the tissues had been completely dissolved as confirmed using a light microscope.

Once the tissues had been completely dissolved, the contents of the well were moved to a 50 ml tissue culture flask containing 5 ml of 15% FCS (fetal calf serum) in RPMI. We made the 15% FCS-RPMI by supplementing RPMI with 15% FCS (heat inactivated for 60 minutes at 56° C.), 10 ml HEPES buffer, 5 ml L-Glutamine, 5 ml vitamin (GIBCO) solution, 5 ml antibiotic/antimicotic solution (GIBCO), 5 ml sodium pyruvate solution, 5 ml non-essential amino acids (Mediatech), and 0.5 ml 2-mercaptoethanol. After thorough mixing, the reagent was filtered using 0.22 um filters and stored at 4° C.

The flask was then incubated at 37° C. in a 5% $CO_2$ water-jacketed incubator until confluent monolayers were obtained. This usually took about a week of incubation.

Following incubation, adherent cells were detached by adding 10 ml of trypsin-EDTA solution and incubating the flask for five minutes at 37° C. We nudged the flask gently with our palm to detach loosely attached cells. We then transferred the contents of the flask to a 15 ml falcon tube and added to the tube 10 ml of 15% FCS-RPMI. We then centrifuged for 5 minutes at 1500 rpm at room temperature.

We decanted the media and resuspended the cells with 10 ml of 15% FCS-RPMI. We then counted the cells for record purposes, and froze down some cells in 10% DMSO (dimethyl sulfoxide) and stored them at −80° C. until use (e.g. using the procedures of section E below). The remaining cells were maintained in culture in 15% FCS-RPMI (approximately $10^5$ cells/ml) at 37° C., in a 5% $CO_2$ water-jacketed incubator.

B. GDFL In Wells

To conduct a proliferation analysis, plates containing the graft-derived cells were prepared one day before obtaining the peripheral blood lymphocytes. We prepared enough wells in order to obtain triplicate measurements for each condition.

GDFL cells were detached from tissue culture flasks with 5ml trypsin-EDTA solution. They were then incubated in the solution for 5 minutes at 37° C. in the 5% $CO_2$ water-jacketed incubator. Following the incubation, the flask was nudged gently with the palm to again detach loosely attached cells. The contents of the flask were added to a 15 ml falcon tube along with 10 ml of 15% FCS-RPMI to resuspend the cells.

We then centrifuged for 5 minutes at 1500 RPM at room temperature and decanted the media followed by resuspending the cells with 10 ml of 15% FCS-RPMI. This procedure was then repeated again. We counted and adjusted the cell number to 25,000 cells/ml.

Five thousand GDFL cells were added to each well of 96-well flat-bottom tissue culture plates. We then incubated the plates for 16 hours at 37° C. in a 5% $CO_2$ water-jacketed incubator.

C. Preparation Of Peripheral Blood Lymohocytes (PBL)

Lymphocytes were isolated from the blood of graft recipients post-transplantation. We drew 4 ml of whole blood from the recipients and placed it into sodium heparin-containing vacutainer tubes. We carefully layered the blood on 4 ml of Ficoll-Histopaque. We then centrifuged the blood through the Ficoll-Histopaque layer for 30 minutes at 1500 rpm at room temperature.

We then gently aspirated the PBL layer and placed it in a fresh 15 ml falcon tube. We then added 10 ml of 15% FCS-RPMI. We then centrifuged again for 5 minutes at 1500 rpm at room temperature.

After centrifugation, we decanted the supernatant and the cells were resuspended in 10 ml of 15% FCS-RPMI. If after centrifugation red blood cells were still visible, we then resuspended the cells in about 2 ml of cold ACK buffer ($NH_4Cl$, $KHCO_3$, $Na_2EDTA$) and incubated for 2 minutes on ice. After incubation, we added 8 ml of 15% FCS-RPMI. The centrifugation steps were then repeated twice.

Contaminating adherent cells were removed by transferring the cells to a 50 ml tissue culture flask and incubating for 15 minutes at 37° C. in a 5% $CO_2$ water-jacketed incubator. After incubation, we aspirated the nonadherent cells into a fresh 15 ml falcon tube, counted the cells and adjusted the cell number to $2\times10^6$ cells/ml.

D. Proliferation Analysis

We aspirated media from wells containing the GDFL cells and added 100 $\mu$l of 15% FCS-RPMI and reaspirated. This was repeated again.

We then added 100 $\mu$l of PBL suspension ($2\times10^5$ cells) to 6 different wells. We then added to only 3 wells 100 $\mu$l of interleukin-2. The IL-2 was prepared in 15% FCS-RPMI, in a final concentration of 20 units/ml. Those wells that did not receive the IL-2 solution received 100 $\mu$l of 15% FCS-RPMI. Control wells were provided containing GDFL cells±the IL-2 solution. For a third party control (nonspecific response) PBLs were added to wells containing third party GDFL cells (graft cells derived from a subject other than the donor)±IL-2.

Each plate was then incubated for 3 days at 37° C., in a 5% $CO^2$ water-jacketed incubator. On day 4, we added 25 $\mu$l [$^3$H] thymidine (2 $\mu$Ci/25 $\mu$l in 15% FCS-RPMI) to all wells, and the incubation resumed for 16 hr. at 37° C. in a 5% $CO_2$ water-jacketed incubator. After incubation, cells were harvested from the wells onto a glass fiber filter using a Filtermate Harvester.

We then allowed the filter to air dry by hanging in a fume hood. [$^3$H] thymidine uptake by the cells (proliferation) was measured by reading the radioactivity of the filter using a Matrix[96] Direct Beta Counter.

The mean (average) radioactivity of the triplicate measurements was calculated for each treatment. The net mean radioactivity was determined by subtracting the mean radioactivity values of wells containing only GDFL cells from the mean values of wells containing PBLs+GDFL cells. The percent response of PBLs to GDFL cells was calculated as previously recited.

We have prepared GDFL lines from humans and monkeys (rhesus monkeys). We have also successfully monitored the transplantation status of rhesus monkey transplant recipients via the above techniques.

We are now in the process of monitoring the immunological status of humans using this technique. In any event, rhesus monkeys are a well established model for examining strategies for promoting transplantation tolerance in humans and for elucidating mechanisms involved in graft acceptance or rejection in humans. In this regard, the rhesus monkey's immune system is similar to that of humans.

E. Long-Term Storage Of GDFL

GDFL cells can be decanted and detached from the flask by adding 5 ml of EDTA-trypsin solution. The flask is then incubated for 5 minutes at 37° C. in a 5% $CO_2$ water-jacket incubator.

Following the incubation, the flask is gently nudged with the palm to detach loosely attached cells. The contents of the flask are then transferred to a 15 ml falcon tube to which is added 10 ml of 15% FCS-RPMI.

We then centrifuged the cells for 5 minutes at 1500 rpm at room temperature, decanted the media and resuspended the cells with 10 ml of 15% FCS-RPMI. If desired, these steps can be repeated.

We then resuspend the pellet in 15% FCS-RPMI. We then place 450 $\mu$l of cell suspension in cryovials containing 450 $\mu$l of FCS. The cryovials were placed on ice for 30 minutes. We then, using a pipetman, gently added 100 $\mu$l of DMSO to the bottom of each cryovial. Immediately prior to the freezing, we then inverted the tubes gently 5–6 times and stored at −80° C.

Results

We observed that [$^3$H] thymidine uptake in control PBLs (obtained from the blood of non-transplanted monkeys) that were incubated with GDFL cells was markedly less in the absence of IL-2 than in the presence of IL-2. This is consistent with the PBLs in controls not being sensitized to the GDFLs. The increase in [$^3$H] thymidine uptake in PBLs in the presence of IL-2 compared to that in the absence of IL-2 is most likely due to the activation of the cells as a result of IL-2 binding to its cell-bound receptor.

In accordance with the present invention, similar results were obtained when lymphocytes from non-rejecting recipients, confirmed by serum creatinine and by histological analysis, were incubated with GDFL cells from the donor or from third-party primates.

In contrast, [$^3$H] thymidine uptake in cells obtained from recipients experiencing rejection was relatively high even in the absence of IL-2. Due to the large variation in the basal level of [$^3$H] thymidine uptake in PBLs from different transplants, it was not possible (in a statistically valid manner) to separate the recipients into two distinct groups based only on [$^3$H] thymidine uptake in response to GDFL cells in the absence of IL-2.

Therefore, we examined whether the difference in [$^3$H] thymidine uptake in the absence and in the presence of IL-2 would be useful to discriminate between non-rejecting and rejecting animals. The % IL2−/IL2+ response of PBLs obtained from non-rejecting and rejecting animals was correlated against serum creatinine.

The initial experiments involved kidneys from MHC-mismatched donors. Statistical analysis indicated that the % IL2−/IL2+ response to donor GDFL cells strongly correlated with serum creatinine (correlation coefficient=0.64, p-value < 0.002, n=29). See FIG. 1. The higher the proportion, the greater the degree of rejection.

Figure 2:
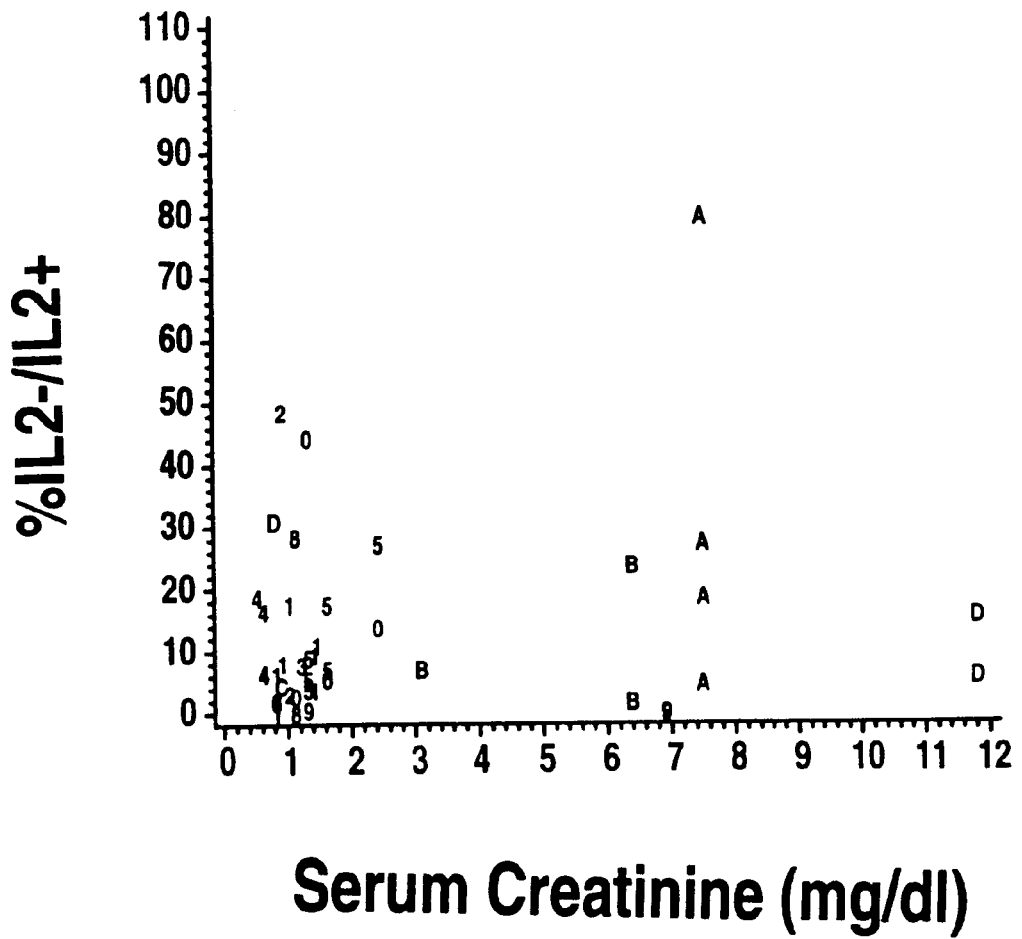
FIG. 2 depicts the % IL-2-/IL-2+ response of peripheral blood lymphocytes obtained from animals plotted against serum creatinine where the response is to third party GDFL cells.

In contrast, and importantly, there was no significant correlation between % IL2−/IL2+ response to third-party GDFL cells and serum creatinine (correlation coefficient=0.074, p-value 0.64, n=42). See FIG. 2. Thus, the response detected by our assay was donor-specific.

To further analyze the data we divided the data into two groups according to a cut off value for creatinine: group #1 contained data obtained from primates with serum creatinine < 2, and group #2 contained data from primates with serum creatinine of > 2. In group #1 mean % IL2−/IL2+ response to donor GDFL cells was not significantly different from that to third-party GDFL cells (p-value < 0.39).

In contrast, in group #2 mean % IL2−/IL2+ response to donor GDFL cells was significantly more than that to third-party GDFL cells (p-value < 0.001). Importantly, the response of group 1 to donor GDFL cells was significantly less than the response of group 2 to donor GDFL cells (mean % IL2−/IL2+± SD was 13±14 and 77±28, respectively; p<0.001).

TABLE 1

Mean ± S.D. % IL2−/IL2+ Response vs. Serum Creatine

| Group # | Creatinine | GDFL Cells Donor | GDFL Cells Third Party | p-value |
|---|---|---|---|---|
| 1 | <2 | 13 ± 14(21) | 11 ± 13(29) | 0.39 |
| 2 | ≧2 | 77 ± 28(8) | 16 ± 23(13) | 0.001 |

Numbers in parentheses indicated number of tests.

We also analyzed the data by dividing the data into the following two groups according to the Banff classification of biopsy pathology: data for group #1 were obtained from primates that suffered from acute rejection 1A (AR1A); data for group #2 were obtained from primates with acute rejection 1B (AR1B). In group #1 mean % IL2−/IL2+ response to donor GDFL cells was not different from that to third party GDFL cells (p-value < 0.84). Yet, in group #2 mean % IL2−/IL2+ response to donor GDFL cells was significantly more than that to third party GDFL cells (p-value < 0.01). Indeed, the response of group 1 to donor GDFL cells was significantly less than the response of group 2 to donor GDFL cells (mean % IL2−/IL2+± SD was 13±10 and 81±30, respectively; p<0.004). These data show that the increase in the percentage of IL2−/IL2+ correlated with the increase in serum creatinine and with the severity of the pathological changes within the graft.

TABLE 2

Mean ± S.D. % IL2−/IL2+ Response vs. Histology

| Group # | Biopsy | DFL Cells Donor | DFL Cells Third Party | p-value |
|---|---|---|---|---|
| 1 | AR1A | 13 ± 10(8) | 16 ± 17(11) | 0.84 |
| 2 | AR1B | 81 ± 30(5) | 22 ± 25(8) | 0.01 |

A useful diagnostic test preferably has both a high sensitivity and specificity. We thus also analyzed the data by considering a % IL2−/IL2+ value of greater than 25 as a positive indication of severe rejection. Rejection was defined as a creatinine value greater than 2. For donors, the ratio had a sensitivity of 100% for detecting rejections (8/8), and a specificity of 86% (18/21) for detecting non-rejections. On the other hand, for third-party the ratio had a sensitivity of only 23% (3/13) and a specificity of 86% (25/29).

This difference in sensitivity and specificity between the donor and third-party was quite statistically significant (p=0.007, Breslow-Day test). PBLs from rejecting animals failed to take up [$^3$H] thymidine in the absence of GDFL cells, indicating that [$^3$H] thymidine uptake by PBLs is due to the activation of PBLs by the interaction with alloantigens on GDFL cells. Accordingly, there was no [$^3$H] thymidine uptake when PBLs from rejecting animals and donor GDFL cells were separated by cell-impermeable membranes, confirming that cell-cell contact is required for [$^3$H] thymidine uptake by PBLs.

Notably, one recipient that showed high creatinine levels had graft failure attributed to glomerulonephritis. Our assay showed a percentage IL2−/IL2+ response for this recipient that was similar to that seen in non-rejecting animals. Thus, our assay detects graft failure due to rejection but does not detect failure due to nonallospecific immune injury.

The specificity of our assay was also examined by studying the responsiveness of recipient PBLs to donor lymphocytes. PBLs that responded strongly to donor GDFL cells failed to respond to stimulation by the donor's lymphocytes. Thus, our assay can detect graft-specific responses that otherwise cannot be detected in assays such as Mixed Lymphocyte Reaction assay where donor lymphocytes are used as stimulators.

Monitoring

Over 25% of human organ transplant patients on immunosuppressive protocols develop rejection in the first six months post-transplant. Thus, a human patient who receives an organ transplant should preferably be tested using this assay about once every other week for the first year after transplantation.

Advantages

The present invention has the following advantages:

1. It uses GDFL cells rather than donor circulating lymphocytes that may not bear graft-specific antigens. The GDFL cells can be propagated almost indefinitely in culture and can be safely frozen. Before a transplant is completed a GDFL cell line specific to it can be prepared without any invasion of the recipient. This could be a standard procedure immediately prior to transplantation. Alternatively, the biopsy could be conducted post-transplantation.

2. The monitoring specimens are preferably blood lymphocytes from the transplant recipient. Obtaining whole blood is a standard and relatively non-invasive procedure.

3. The assay is designed to better discriminate between responses of graft-sensitized cells and those cells stimulated by infections.

Other Embodiments

While the initial experiments were made on recipients of kidney transplants, the present invention is suitable for use in monitoring the condition of recipients of other organ transplants (e.g. liver, skin, heart, lung, etc.). In this regard, we also isolated GDFL cells from the lung. Moreover, similar amounts of other cytokine growth factors such as IL-4 and transforming growth factory can be substituted for IL-2.

Also, the lymphocytes need not be obtained from whole blood. Instead, they may be obtained from any other sample taken from the recipient post-transplant, other than a sample from the transplanted organ.

While a [$^3$H] thymidine uptake proliferation assay is preferred, other known assays to assess such activation are also contemplated.

Thus, the invention is not to be limited to the specific embodiments described above. Rather, it should be provided its full scope as described in the following claims.

Industrial Applicability

The invention provides methods for monitoring the immunological status of transplant recipients.

We claim:

1. A method for monitoring the immunological status of a human transplant recipient who has received a transplanted organ, comprising the steps of:
    as step X, in the presence of a first concentration of an externally supplied quantity of a specified cytokine growth factor, exposing fibroblast cells derived from the organ to post-transplant lymphocytes from the recipient (other than lymphocytes from said organ);
    determining the extent to which the step X lymphocytes are immunologically activated by exposure to the step X cells;
    as step XX, in the absence of an externally supplied quantity of said specified cytokine growth factor, or in the presence of a concentration thereof which is less than that used in step X, exposing fibroblast cells derived from the transplanted organ to post-transplant lymphocytes from the recipient (other than lymphocytes from said organ);
    determining the extent to which the step XX lymphocytes are immunologically activated by exposure to the step XX cells; and
    determining from the extent to which the immunological activation is greater in step X than in step XX the extent to which the transplanted organ is being rejected by the recipient.

2. The method of claim 1, wherein the cytokine for both step X and step XX is selected from the group consisting of interleukin-2, interleukin-4 and transforming growth factor-β.

3. The method of claim 2, wherein the specified cytokine for both step X and step XX is interleukin-2.

4. The method of claim 2, wherein the lymphocytes used in both step X and step XX are peripheral blood lymphocytes.

5. The method of claim 3, wherein the determination of the immunological activation status of the lymphocytes is made using a proliferation assay.

6. The method of claim 5, wherein [$^3$H] thymidine uptake is used to assess lymphocyte activation in the proliferation assay.

7. The method of claim 1, wherein the fibroblast cells were derived from a biopsy of the organ taken post-transplantation.

* * * * *